United States Patent
Thomas et al.

(10) Patent No.: US 9,953,732 B2
(45) Date of Patent: Apr. 24, 2018

(54) RADIATION PROTECTION CURTAIN

(71) Applicant: Wipotec Wiege- und Positioniersysteme GmbH, Kaiserslautern (DE)

(72) Inventors: Werner Thomas, Hochspeyer (DE); Manuel Allmann, Fischbach (DE)

(73) Assignee: Wipotec Wiege- und Positioniersysteme GmbH, Kaiserslautern (DE)

( * ) Notice: Subject to any disclaimer, the term of this patent is extended or adjusted under 35 U.S.C. 154(b) by 0 days.

(21) Appl. No.: 15/488,862

(22) Filed: Apr. 17, 2017

(65) Prior Publication Data

US 2017/0301424 A1    Oct. 19, 2017

(30) Foreign Application Priority Data

Apr. 18, 2016    (DE) .......................... 10 2016 107 126

(51) Int. Cl.
  *G21F 3/00*    (2006.01)
(52) U.S. Cl.
  CPC ...................... *G21F 3/00* (2013.01)
(58) Field of Classification Search
  USPC ................. 250/515.1, 517.1, 519.1
  See application file for complete search history.

(56) References Cited

U.S. PATENT DOCUMENTS

| | | | |
|---|---|---|---|
| 6,304,629 B1 | 10/2001 | Conway et al. | |
| 2006/0151750 A1* | 7/2006 | Eder | G21F 1/12 252/478 |
| 2011/0058650 A1 | 3/2011 | Makino et al. | |
| 2015/0262720 A1 | 9/2015 | Weed | |
| 2017/0032858 A1 | 2/2017 | King | |

FOREIGN PATENT DOCUMENTS

| | | |
|---|---|---|
| EP | 2194373 A1 | 6/2010 |
| EP | 2930719 A1 | 10/2015 |
| JP | 2002228601 A1 | 8/2002 |
| JP | 2015059813 A | 3/2015 |

* cited by examiner

*Primary Examiner* — Kiet T Nguyen
(74) *Attorney, Agent, or Firm* — The Webb Law Firm

(57) ABSTRACT

The invention concerns a radiation protection curtain including at least two layers arranged parallel to each other, for use with a means of transporting objects to be scanned on a production line in a direction through the radiation protection curtain. At least one first layer is configured as a radiation protection layer. This at least one first radiation protection layer is preceded in the transport direction outwards by at least one additional separate stand-alone layer. This at least one additional layer is configured as a mechanical protection layer for the purpose of protecting the radiation protection layer behind it from mechanical effects, and the at least one additional mechanical protection layer includes at least one segment that is located on an already-installed radiation protection layer at predefined positions in such a way that it can be replaced individually.

20 Claims, 5 Drawing Sheets

RADIATION PROTECTION CURTAIN

CROSS-REFERENCE TO RELATED APPLICATION

This application claims priority to German Patent Application No. 10 2016 107 126.9 filed Apr. 18, 2016, the disclosure of which is hereby incorporated in its entirety by reference.

BACKGROUND OF THE INVENTION

Field of the Invention

This invention concerns a radiation protection curtain, in particular for shielding against X-ray or gamma radiation. These types of radiation protection curtains are usually used to cover the entrance or exit of a room in which objects are scanned using radiation. In the more recent past, in addition to the types of radiation mentioned above, terahertz radiation and/or terahertz wavelengths have also come to be used for scanning, in the form of body scanners, for example.

Description of Related Art

In practice, X-ray radiation in particular is being used more and more frequently in main areas, such as in airport security to scan the contents of suitcases. X-ray radiation is also used in medicine for some treatments. The X-rays penetrate the body and show certain disorders, such as broken bones. X-ray radiation is also used in industrial inspection technology. Due to the health risks to personnel who operate radiation systems, protection against unacceptable radiation levels is necessary.

One common industrial solution for this is the use of radiation protection curtains, which preferably allow an object to be scanned to move through a radiation protection curtain, on a conveyor belt, for example. In this way, in particular, multiple objects can be inspected in sequence (such as packaged products), wherein the objects are transported in succession through the radiation protection curtain (entrance) into a radiation-shielded scanning room and preferably carried on continuously through another radiation protection curtain (exit) out of the scanning room.

EP 2 194 373 A1, for example, describes a radiation protection curtain whose shielding elements form an entire unit. These elements are hung on horizontal bars. A disadvantage is that such a radiation protection curtain can be damaged by frequent mechanical contact with objects being transported through it. Even if only one element is damaged, the entire unit must be replaced. In addition, the contact surfaces of the holders on the bars must withstand a high friction force, in order to counteract the force generated by an object being carried through the protective curtain and the related swinging of the protective curtain in the transport direction as well as upward and/or to the side.

EP 2 930 719 A1 also describes a radiation protection curtain that has multiple long straight vertical shielding elements adjacent to each other. These are hung on a horizontal bar. If one element is damaged, many other elements must be removed in order to replace one element.

Mechanical damage to a radiation protection curtain, especially surface wear and with it the risk of a radiation leak, as well as the occurrence of undesirable or even hazardous wear (such as lead dust) and the risk of contamination, especially to food, are all possible problems when scanning multiple objects (transported on a conveyor belt, for example) on a production line. For example, objects or products to be scanned can have sharp edges, which on an industrial mass production line strike the shielding element many times per minute in the same place. However, any damage that occurs absolutely must be rectified in order to prevent radiation from escaping.

An objective of this invention is to prevent the problems described above and provide a radiation protection curtain that resists rapid wear.

SUMMARY OF THE INVENTION

The invention achieves this goal by means of a radiation protection curtain.

A mechanical protection layer, immediately preceding (when viewed in the transport direction) and parallel to the actual radiation protection layer and perpendicular to the transport direction, can nearly or fully prevent damage (wear, holes, cracks, etc.) to the most cost-intensive radiation protection layers.

Functional separation of radiation protection and mechanical protection (against damage such as cracks, holes, wear, etc.) also offers the advantage of being able to select the optimal material for each type of layer. This means that the material for the radiation protection layer can be selected without regard for mechanical damage. Likewise, the material for the mechanical protection layer can be selected without regard for a radiation blocking characteristic and can focus on mechanical damage prevention alone. Accordingly, with the invented solution the material selection for the mechanical protection layer can be optimal and can even include a coating, for surface hardness and type (smoothness), friction coefficient, and/or crack resistance, for example, which allows objects to move through without causing wear. Examples of possible materials for mechanical protection layers include sheets of metal or plastic in particular, as well as woven fibers or braided materials.

Use of the invention can prevent damage to the radiation protection layer itself caused by frequent mechanical contact with 200-300 packages per minute, as occurs during an industrial operation, for example, with objects being transported through a radiation protection curtain.

The independent mechanical protection layer that is separate or divided from the radiation protection layer consists of at least one segment that with smaller dimensions than the radiation protection layer. The at least one mechanical protection segment is placed on the radiation protection layer and is replaceable, so that, in the event of significant damage (hole, crack, etc.) to the mechanical protection segment, before any related damage occurs to the radiation protection layer behind it, the mechanical protection segment can easily and efficiently be replaced or exchanged with an undamaged segment. Time-intensive disassembly or even dismantling of the entire radiation protection curtain is preferably not necessary.

Because the at least one mechanical protection segment has smaller dimensions (width and/or height) than the radiation protection layer, one or more segments can advantageously be placed only at locations (in particular areas of probable contact with objects) where mechanical damage is likely to occur. In this way, depending on the transport mode (single line or multiple lines) and on the type of objects to be scanned on a production line, the radiation protection curtain can be enhanced as needed with mechanical segments installed in advance, without having to cover the entire width and/or height of the radiation protection layer in any case. This offers the advantage that a force in opposition to the transport direction and affecting the objects, caused by deadweight and by the necessary swinging of the radiation protection curtain during transport through the radiation-shielded space, can be limited to just what is necessary.

For placement of one or more segments at the desired locations on the radiation protection layer, overhead free spaces can be provided, for example, on a common mounting hanger or attachment unit on a rod (placed crosswise to the transport direction). Segments can be hung in these free spaces as needed.

It is also conceivable, of course, to place detachable segments directly on the surface of the radiation protection layer, by means of hanging, clipping, etc., for example, wherein fastening elements—such as hooks, loops, rings, carabiners—can be provided on the surface of the radiation protection layer that are complementary to the corresponding fastening elements provided on the segments. It is also possible here to place mechanical protection segments not only in their sideways positions (crosswise to the transport direction) but also at various heights, immediately adjacent or preferably directly on (in contact with the surface of) the radiation protection layer in a variety of desired positions.

In a preferred embodiment of the invention, the mechanical protection segments are provided in a variety of dimensions (width and/or height and/or thickness) in the form of a component system (modular segments), so that it can be optimized for all conceivable objects and their locations. This has the advantage of guaranteeing the best possible protection against damage to the radiation protection layer, without affecting transport of the objects or their positions.

In a preferred embodiment of the invention, the radiation protection curtain is configured as a protective curtain against X-ray or gamma radiation, because specifically these types of radiation are considered especially hazardous to the health of people (and animals). Obviously the invented radiation protection curtain can also be used with other radiation types or wavelengths, where radiation emission is undesirable or its effect needs to be limited. This makes it possible to limit the effect and extent of other types of radiation (terahertz, gigahertz, UV, and other radiation types), such as terahertz radiation in body scanners, with a radiation protection curtain according to the invention for a given space.

In addition to the described segmented, modular configuration of the mechanical protection layer with the component option using segments with varying dimensions, the radiation protection layer can also consist of multiple segments, preferably side-by-side with each other, or can be assembled and mounted in component form. Here it is preferably possible to adjust the dimensions of the radiation protection layer to fit the particular situation (width of the conveyor belt, for example), especially concerning the side-to-side dimensions and therefore crosswise to the transport direction of objects through the radiation protection curtain.

In one particular embodiment of the invention, the upper edges of one or more segments of the radiation protection layer can have a first lower joint part, in the form of hooks, sockets, or loops, through which a complementary upper joint part (bolt, pin, wire, rod, etc.) runs. If the aforementioned first lower joint parts have a closed cross-section (ring-shaped), corresponding segments for a particular application are selected, assembled, and all mounted before the matching radiation protection layer is mounted.

On the other hand, if the first lower joint parts do not have a closed cross-section, but rather are configured with a break (facing downward, for example), the segments can also be changed or exchanged later, if necessary, for a particular application or for maintenance purposes. This allows individual segments to be removed from an already installed or hung protective curtain (hanging from above, for example) and another segment or segments to be hung after that.

In another embodiment of the invention, the at least one segment of the mechanical protection layer has a second lower joint part that matches the upper joint part, of a type such that the mechanical protection layer or its at least one segment is swivel-mounted like the radiation protection layer in the transport direction.

In a specific embodiment of the invention, the at least one mechanical protection layer is configured to be hung in free spaces provided in the first lower joint part of an already-installed radiation protection layer. Here the second lower joint part of the mechanical protection layer can have a profile that extends upward and is open downward, for example.

To facilitate the transport of the objects to be scanned through the radiation protection curtain, the segments of the radiation protection layer can consist of multiple separate slats next to each other, which are mounted so that they swivel individually.

The at least one radiation protection layer and/or the at least one mechanical protection layer are preferably configured to be flexible, in particular bendable. Bendable here means that there are no joints in the mechanical protection layer. (Only the mounting hanger can have one or more joints.) In addition, the radiation protection layer and the mechanical protection layer are preferably configured to move separately from each other.

BRIEF DESCRIPTION OF THE DRAWINGS

The invention is described below in relation to an exemplary embodiment illustrated in the drawings.

The drawings show.

DETAILED DESCRIPTION OF THE INVENTION

Figure 1:
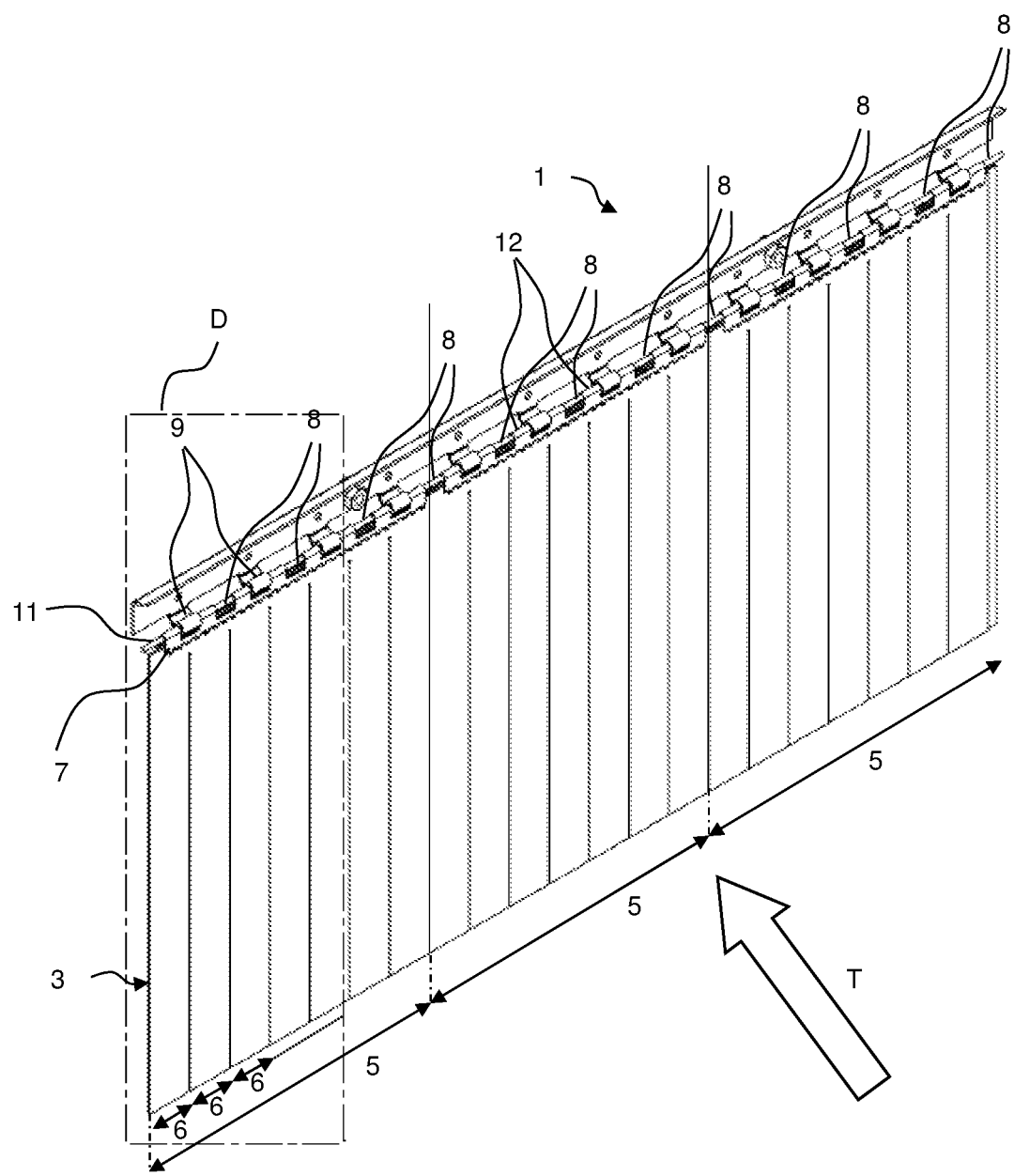
FIG. 1 a perspective representation of an invented radiation protection curtain with no mechanical protection layer.
Figure 2:
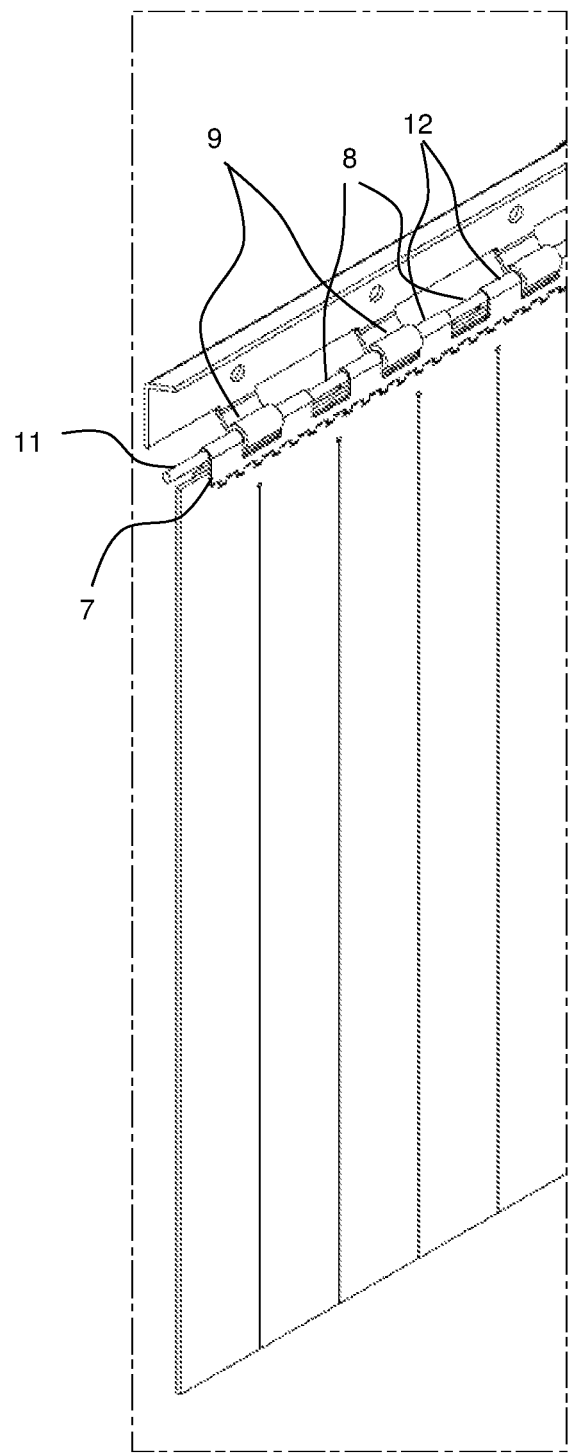
FIG. 2 an enlarged detail view of section D from FIG. 1.

As shown in FIGS. 1 and 2, the invented radiation protection curtain 1 consists of at least one segment 5 (in the example, three segments) of a radiation protection layer 3 with a modular configuration. The rectangular-shaped segments 5 are placed side-by-side, crosswise to a transport direction T for objects to be scanned (not shown) moving through the protection curtain, secured on their upper edges by a first lower joint part 7 to a bar 11. The bar 11 is placed inside an upper joint part 9, so that the radiation protection curtain 1 can be fastened crosswise to the transport direction T (for the objects to be scanned on a production line) over a conveyor belt that is not shown in the drawing and provides radiation protection coverage to the entrance and/or exit (in height and width) of a radiation-shielded space, also not shown in the drawing.

By means of the hinge-type connection at the top edge of a segment 5, that segment 5 can swing around the bar 11 so that by swinging in the direction of the transport direction T and also upward (and/or to the side), objects can pass through the protective curtain. After the objects pass through, the at least one segment 5 swings back into the exit position shown in FIG. 1, in which side-by-side segments 5 are next to each other and prevent undesirable radiation, in particular X-ray radiation, from escaping.

Each segment 5 of the radiation protection layer 3 consists of multiple (for example, seven) slats 6. The material for the segment 5 can also be flexible as well as stiff, in particular made bendable so that individual side-by-side slats 6 of a segment 5 can be deflected in the transport direction independently of each other.

The segment 5 is fastened on its upper edge to the first lower joint part 7, for example pressed in with appropriate tools, and has multiple (eight, in the example) fastening areas in the form of clamps 12 that grip the bar 11. Accordingly, it is possible to hang a segment 5 in one on the bars 11 that run through the upper joint part 9 from above (or diagonally above). On the other hand, if the cross-section of the bar 11 is enclosed by the fastening areas 12, the bar 11 must be run through the joint parts 9 and 7 afterward.

As shown in FIGS. 1 and 2, on the upper edge in the first lower joint part 7 there are additional (four, in the example) free spaces 8 that are not part of the fastening areas of the upper joint part 9. These free spaces 8 (located between the connecting points of the upper joint part 9) are used in the arrangement according to the invention for a separate mechanical protection layer 13 (see FIG. 3) coplanar to the radiation protection layer 3, which preferably can be configured to be flexible, in particular bendable. As shown, the free spaces 8 are laterally equidistant, with a gap of 20 mm between them, for example, so that a segment 15 (see FIG. 3) can be hung in a precise position (spaced by that distance, in this case) as needed.

Figure 3:
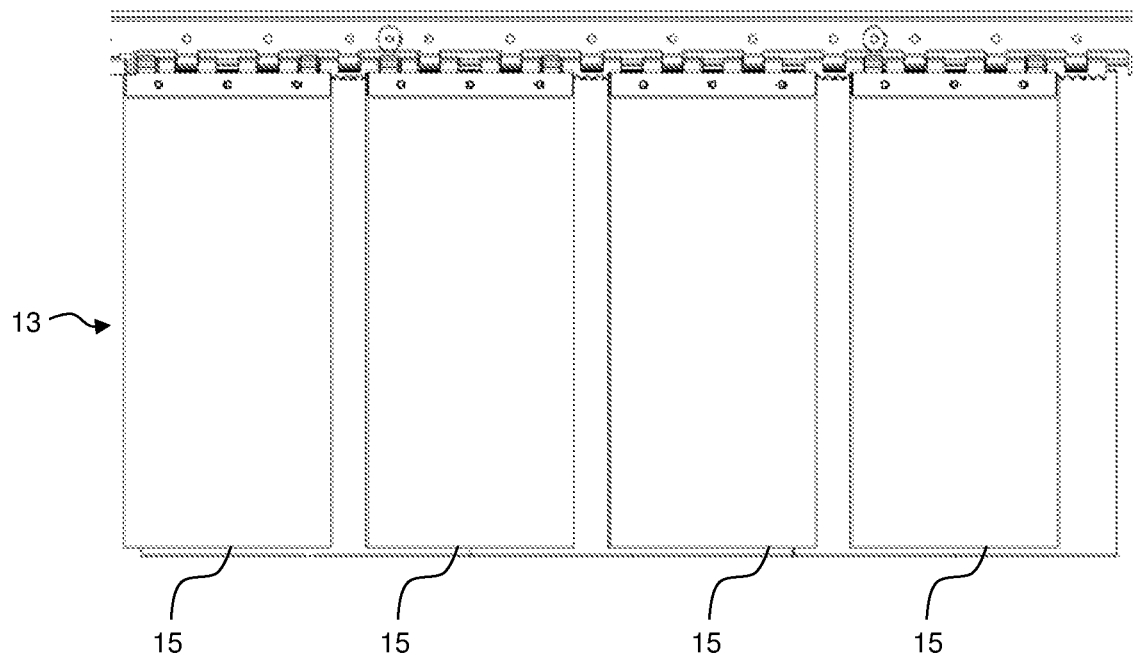
FIG. 3 a front view of a radiation protection curtain as in FIG. 1 with four hanging segments of a mechanical protection layer.

FIG. 3 shows a radiation protection curtain, complete and mounted according to the invention, with four side-by-side segments 15 of the mechanical protection layer 13 in front of a radiation protection layer 3 (described in FIGS. 1 and 2) located immediately behind it in the transport direction.

Unlike the radiation protection layer 3, lateral spacing between the segments 15 of the mechanical protection layer 13 is possible and is permissible in respect of a minimum lateral dimension of objects (spacing smaller than the minimum lateral dimension), because no radiation can escape through these gaps.

Figure 4:
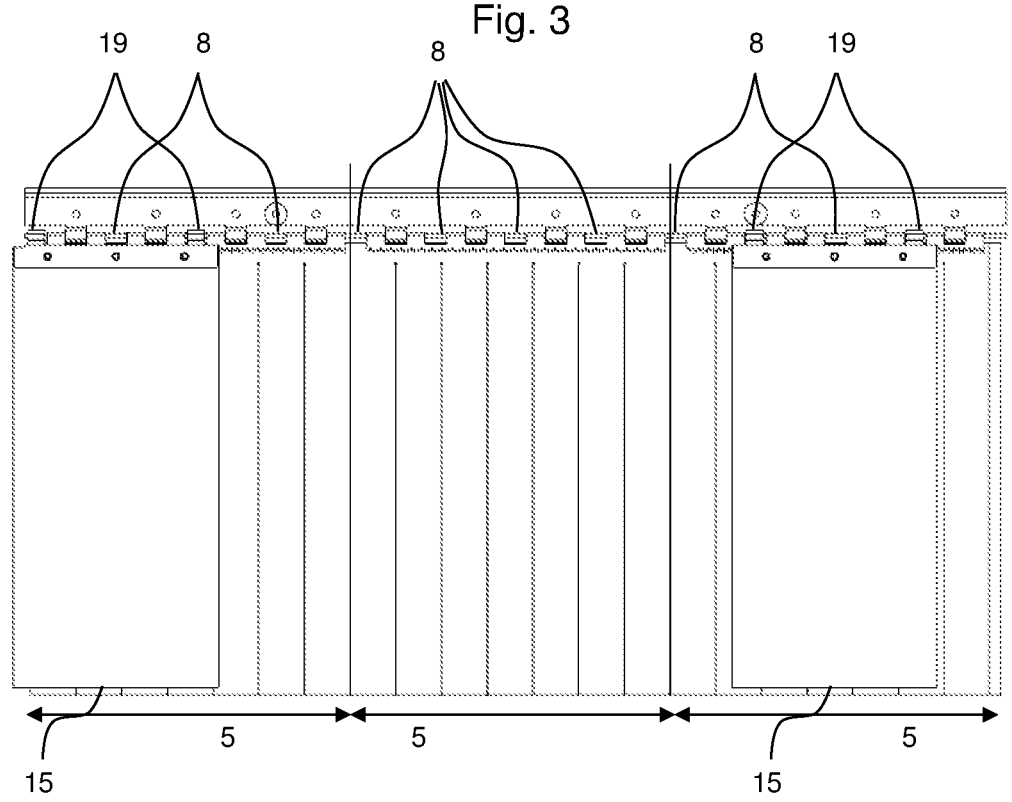
FIG. 4 a front view of a radiation protection curtain as in FIG. 1 with two outer hanging segments of a mechanical protection layer.

As shown in FIG. 4, even just individual segments 15, for example the outer ones, can be hung, for example with two lines of objects having similar dimensions and spacing between lines. As shown specifically in FIGS. 5 and 6, each of the segments can be hung, as needed, with an adjacent free space 8 in a location moved to the left or to the right, so that when the corresponding need arises (object sizes or line width, number of lines and line spacing), there can be a response with correspondingly altered positions and/or numbers of the segments 15.

These segments 15 absolutely do not all have to be the same, but rather can differ with respect to their lateral dimensions in particular. For example, a component system is possible in which the segments 15 have different widths, such as widths differing from each other by 2 cm in a repeating pattern.

The segments 5 of the radiation protection layer 3, which consist of flexible one-ply or multi-ply slats 6 filled with lead dust, for example, can be protected effectively against damage by the hanging segments 15 of the mechanical protection layer 13.

As shown in FIGS. 3-6, the segments 15 of the mechanical protection layer 13 can also be arranged in their side-by-side positions in such a way that they overlap the separations between the side-by-side segments 5 of the radiation protection layer 3 (see in particular the two middle segments 15 in FIG. 3).

In the preferred configuration with individual slats 6 that can flex or in particular bend in the transport direction T (20 mm wide, for example), as soon as a segment 15 is contacted with force by an object in direction T, the slat 6 located behind it moves or swings in direction T with it.

The invented radiation protection curtain 1 is preferably assembled by tool-free hanging of each segment 5 or 15 on the upper joint part 9 or on the bar 11 or free space 8. Here the segments of the radiation protection curtain are all modular and individually replaceable.

If the segments 5 and/or 15 have fastening areas on their first and second lower joint parts 7 and 19 that only grip but do not surround the bar 11, then the segments 15 (of the mechanical protection layer 13) and/or the segments 5 (of the radiation protection layer 3) can also be hung later on a radiation protection curtain 1 that is already installed and can be replaced individually in modular fashion. The segments 15 of the mechanical protection layer 13 are hung in (in the first lower joint part 7) predefined free spaces on the bar 11, which gives them a defined position. This makes it possible to install the segments 15 quickly and easily.

With the type of assembly shown in the exemplary embodiment there are no parts that can be lost. Any screws are needed on the upper joint part 9 only to mount the assembly itself or the upper joint part 9 to a radiation-shielded space, for example.

The invented radiation protection curtain offers the advantage of being able to quickly change individual segments 15 (and possibly also segments 5) to adapt to any objects, in particular package characteristics and radiation intensities (quick configuration of the optimal protection curtain).

LIST OF DRAWING REFERENCES

Figure 5:
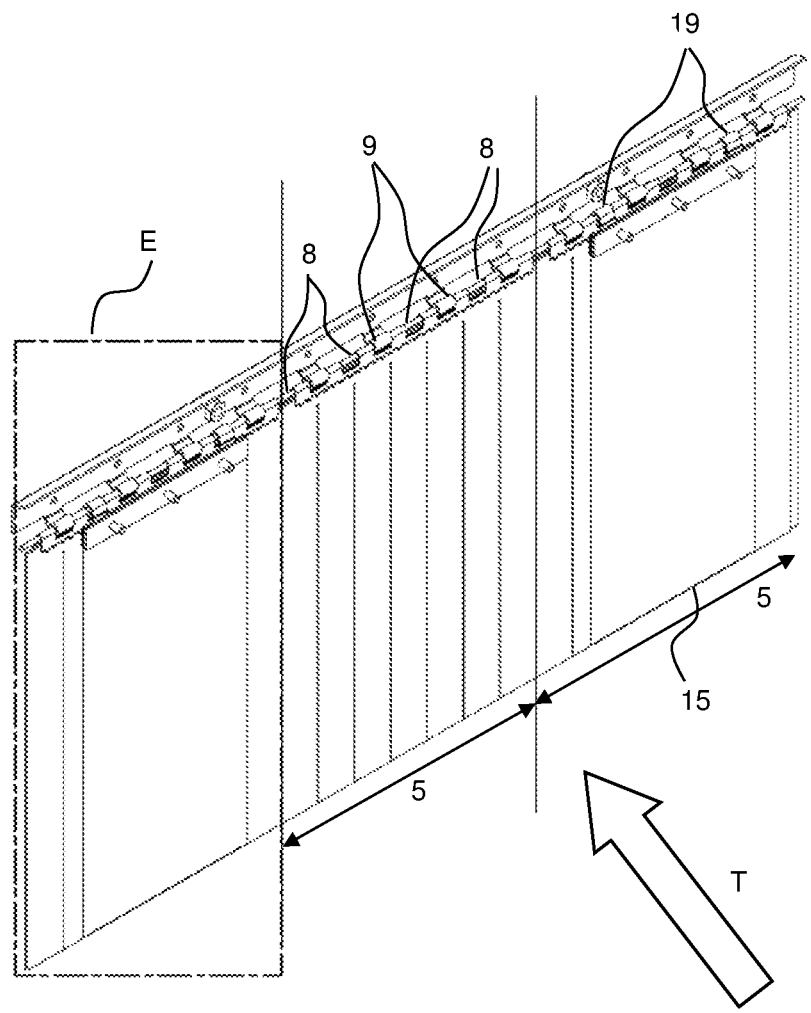
FIG. 5 a perspective view of the radiation protection curtain as in FIG. 4.
Figure 6:
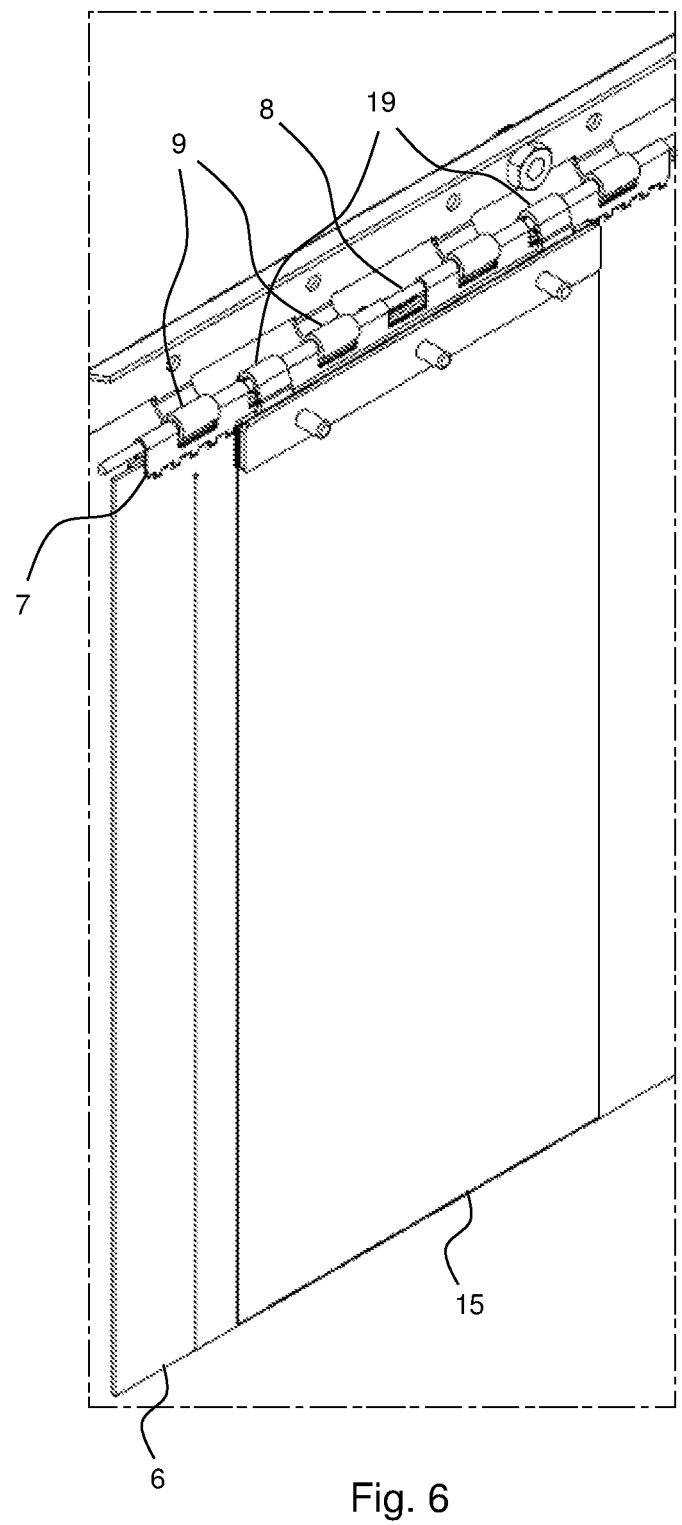
FIG. 6 an enlarged detail view of section E from FIG. 5.

1 Radiation protection curtain
3 Radiation protection layer
5 Segments of the radiation protection layer
6 Slats of segment 5
7 First lower joint part (of the radiation protection layer)
8 Free spaces in the first lower joint part 7
9 Upper joint part
11 Bar
12 Clamp (fastening area)
13 Mechanical protection layer
15 Segment of the mechanical protection layer
19 Second lower joint part (of the mechanical protection layer)
T Transport direction of the objects to be scanned
D Cutout from FIG. 1
E Cutout from FIG. 5

The invention claimed is:

1. A radiation protection curtain comprising at least two layers arranged parallel to each other, for transporting objects to be scanned on a production line in a direction through the radiation protection curtain,
wherein
a) at least one first layer is configured as a radiation protection layer, b) the at least one first radiation protection layer is preceded outwards in the transport direction by at least one additional separate stand-alone layer, c) the at least one additional layer is configured as a mechanical protection layer, used to protect the radiation protection layer behind it from mechanical effects, and d) the at least one additional mechanical protection layer comprises at least one segment, which is located on an already-installed radiation protection layer and can be individually replaced at predefined positions.

2. The radiation protection curtain as in claim 1, wherein the mechanical protection layer is modular and comprises multiple separate segments.

3. The radiation protection curtain as in claim 2, wherein the mechanical protection layer comprises multiple separate segments placed crosswise to the transport direction and side-by-side next to each other.

4. The radiation protection curtain as in claim 3, wherein the at least one additional mechanical protection layer has smaller dimensions than the radiation protection layer.

5. The radiation protection curtain as in claim 3, wherein the radiation protection curtain is configured as a protection curtain against X-ray or gamma radiation.

6. The radiation protection curtain as in claim 2, wherein the at least one additional mechanical protection layer has smaller dimensions than the radiation protection layer.

7. The radiation protection curtain as in claim 2, wherein the radiation protection curtain is configured as a protection curtain against X-ray or gamma radiation.

8. The radiation protection curtain as in claim 2, wherein the radiation protection layer comprises multiple separate segments placed crosswise to the transport direction and side-by-side next to each other.

9. The radiation protection curtain as in claim 2, wherein the at least one radiation protection layer and/or the at least one mechanical protection layer are hung on an upper joint part with a first lower joint part and a second lower joint part, respectively.

10. The radiation protection curtain as in claim 2, wherein the at least one additional mechanical protection layer can be fastened directly to the radiation protection layer.

11. The radiation protection curtain as in claim 1, wherein the at least one additional mechanical protection layer has smaller dimensions than the radiation protection layer.

12. The radiation protection curtain as in claim 11, wherein the radiation protection curtain is configured as a protection curtain against X-ray or gamma radiation.

13. The radiation protection curtain as in claim 1, wherein the radiation protection curtain is configured as a protection curtain against X-ray or gamma radiation.

14. The radiation protection curtain as in claim 1, wherein the radiation protection layer comprises multiple separate segments placed crosswise to the transport direction and side-by-side next to each other.

15. The radiation protection layer as in claim 14, wherein individual segments of the radiation protection layer are located on an already-installed radiation protection layer so that they can be replaced individually without disassembling the other segments.

16. The radiation protection curtain as in claim 14, wherein the segments of the radiation protection layer comprise multiple side-by-side slats adjacent to each other.

17. The radiation protection curtain as in claim 1, wherein the at least one radiation protection layer and/or the at least one mechanical protection layer are hung on an upper joint part with a first lower joint part and a second lower joint part, respectively.

18. The radiation protection curtain as in claim 17, wherein the at least one mechanical protection layer can be placed, in predefined free spaces provided in the first lower joint part of an already-installed radiation protection layer.

19. The radiation protection curtain as in claim 18, wherein the at least one mechanical protection layer can be hung in the predefined free spaces.

20. The radiation protection curtain as in claim 1, wherein the at least one additional mechanical protection layer can be fastened directly to the radiation protection layer.

* * * * *